United States Patent
Horrobin et al.

(10) Patent No.: US 6,245,811 B1
(45) Date of Patent: Jun. 12, 2001

(54) FATTY ACID ESTERS AS BIOACTIVE COMPOUNDS

(75) Inventors: David Frederick Horrobin, Guildford; Mehar Manku, Carlisle; Austin McMordie, Carlisle; Philip Knowles, Carlisle; Peter Redden, Nova Scotia; Andrea Pitt, Carlisle, all of (GB)

(73) Assignee: Scotia Holdings PLC, Surrey (GB)

( * ) Notice: Subject to any disclaimer, the term of this patent is extended or adjusted under 35 U.S.C. 154(b) by 0 days.

(21) Appl. No.: 09/376,617

(22) Filed: Aug. 18, 1999

Related U.S. Application Data

(62) Division of application No. 08/945,779, filed as application No. PCT/GB96/01052 on May 1, 1996, now abandoned.

(30) Foreign Application Priority Data

May 1, 1995 (GB) .................................................. 9508823
Aug. 21, 1995 (GB) .................................................. 9517107
Mar. 15, 1996 (GB) .................................................. 9605440

(51) Int. Cl.[7] .................................................. A61K 31/225
(52) U.S. Cl. .................................. 514/547; 514/546; 514/549; 514/552; 554/110; 554/223; 554/224; 554/227
(58) Field of Search ........................................ 554/110, 223, 554/224, 227; 514/546, 547, 549, 552

(56) References Cited

U.S. PATENT DOCUMENTS 6,015,821 * 1/2000 Horrobin et al. .................... 514/335

* cited by examiner

*Primary Examiner*—Deborah D. Carr
(74) *Attorney, Agent, or Firm*—Bruce D. Gray, Esq.; Kilpatrick Stockton LLP

(57) ABSTRACT

Compounds of structure (I), and when for use in therapy: where $R_1$ is an acyl group derived from a $C_{16-30}$ fatty acid with two or more cis or trans double bonds and particularly an n-6 or n-3 series EFA or conjugated linoleic acid, or columbinic acid, or parinaric acid and $R_2$ is as $R_1$ the same or different, or any other nutrient, drug or other bioactive residue released as the active in the body and $R_3$ is either hydrogen, fully hydrocarbon, or containing heteroatoms, preferably an alkyl group particularly a $C_1$–$C_4$ alkyl group.

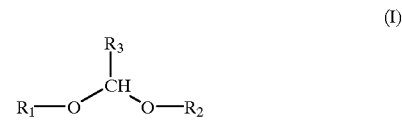

(I)

64 Claims, No Drawings

FATTY ACID ESTERS AS BIOACTIVE COMPOUNDS

This application is a divisional of U.S. application Ser. No. 08/945,779, filed Jan. 26, 1998, now abandoned, which is a 35 U.S.C. §371 application of PCT/GB96/01052, filed May 1, 1996 which claims priority to (1) Great Britain Application No. 9517107.0; (2) Great Britain Application No. 9605440.8; and (3) Great Britain Application No. 9508823.3.

FIELD

The specification relates to the presentation of bioactives, in which term we include a drug, essential nutrient or any other compound to be administered to the human or animal body in therapy or maintenance of health.

In particular, the specification relates to the presentation of such bioactives in a form in which they are lipophilic so that they can pass lipid barriers in the body readily, or to the presentation of two bioactives in the same molecule (where at least one of the bioactives is a fatty acid or fatty alcohol), or to the presentation of bioactives in a form which serves both aims and/or the aims of ready synthesis of such compounds without a chiral centre. From a drug regulatory viewpoint it is a great advantage to have two bioactives presented as a single molecule rather than as two separate entities. There may also be advantages in presenting known bioactives in novel ways. Those advantages include increased lipophilicity, the additive effects of two bioactives which are not normally presented together, and the sometimes synergistic effects of such bioactives.

The invention concerns the linking of bioactives (where at least one bioactive is an unsaturated fatty acid) through certain link molecules, specifically geminal dioxo and geminal amino oxo moieties considered in detail later herein, to yield geminal tripartate drugs, the synthesis of a range of compounds and their use in therapy and/or the maintenance of health.

Geminal Tripartate Mutual Prodrug Concept

Frequently simple ester mutual prodrugs of bioactives are not sufficiently labile in vivo to ensure a sufficiently high rate of conversion of the prodrug to the two desired bioactives. One reason is that for these simple ester mutual prodrugs the ester bond may be resistant to enzymatic attack for either steric or electronic reasons. One way to overcome this problem is to use the geminal tripartate mutual prodrug approach whereby the bioactives are linked via either a geminal dioxo or geminal amino oxo linkage. For example, two bioactive carboxylic acids may be linked as a diester via a geminal dioxo linkage. As outlined in Scheme 1, the first step in the hydrolysis of the general dioxo diester is enzymatic cleavage, either via enzymatic pathway 1 or pathway 2, of one of the mutual bioactive ester bonds with subsequent formation of a highly unstable hydroxymethyl ester which rapidly dissociates in vivo to the other bioactive and an aldehyde. With either pathway both bioactives are generated after only one enzymatic hydrolysis reaction.

A further advantage is the opportunity for simultaneously or approximately simultaneous delivery of two different bioactives. For example, a bioactive alcohol may be coupled to an unsaturated fatty acid as an ester/ether via a geminal dioxo linkage. As outlined in Scheme 2, ester hydrolysis leads to formation of the unsaturated fatty acid and an unstable hemiacetal derivative of the bioactive alcohol which rapidly splits into the free bioactive and an aldehyde.

Scheme 1

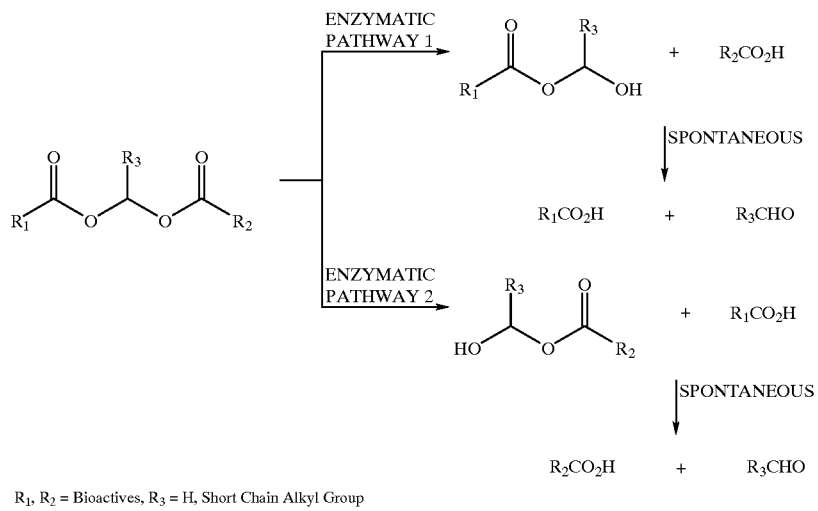

$R_1$, $R_2$ = Bioactives, $R_3$ = H, Short Chain Alkyl Group

Scheme 2

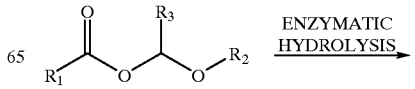

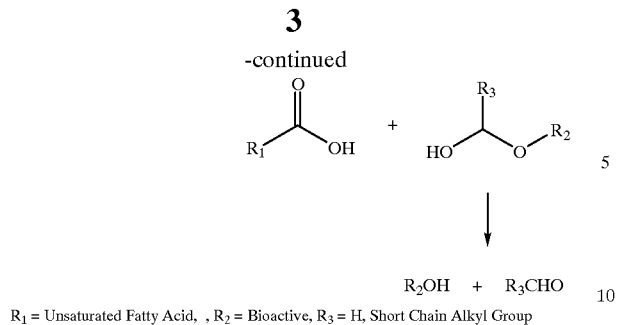

R₁ = Unsaturated Fatty Acid, , R₂ = Bioactive, R₃ = H, Short Chain Alkyl Group

Published Material

The concepts of linking unsaturated fatty acids to bioactives using the geminal dioxo or geminal amino oxo diester approach such as discussed above has received no great attention in the published patent and general literature with the exception of Terumo K.K. in EPA-0 222 155 which link 5-fluoro uracil to alpha linolenic acid, dihomo gamma linolenic acid, or eicosapentaenoic acid through a group —CH(R)-O— where R=methyl etc as, inter alia, anti-cancer agents.

Lipid Barriers

Many drugs act at the cell membrane surface by combining with cell surface receptors, or alternatively are taken into cells by specific transport systems. However, there are many drugs which, while they act within cells by modifying one of many different functions such as nucleic acid functions, the actions of intracellular enzymes, or the behaviour of systems like the lysosomes or the microtubules, are not able to penetrate cells effectively. There may be no receptors and transport systems with which they can link, or these systems may transport the drug into the cell at a less then optimum rate. Equally drugs may penetrate intracellular membranes such as mitochondrial and nuclear membranes at less than optimum rates.

There are other barriers to drug movements which are recognised as important. One of particular significance is the blood-brain barrier, which has many of the characteristics of the cell membrane. There are many drugs which have difficulty in reaching adequate concentrations in the brain because of this barrier. Another is the skin: until a few years ago drugs were applied to the skin only if their purpose was to act on the skin. However, it has been recognised that the skin can be an appropriate route for getting drugs with systemic actions into the body, and as a result more and more compounds are being administered by variations of patch technology.

All three types of barriers, the cell membrane and intracellular membranes, the blood-brain barrier and the skin have an important feature in common, they are substantially composed of lipids. What this means is that they are impermeable to primarily water-soluble drugs unless these drugs can be carried across the membrane by a receptor or transport system. In contrast, lipophilic substances are able to cross the barriers more readily without the need for any specific receptor or transport system.

Classes of Bioactives Requiring Passage Through Lipid Barriers

Drugs whose pharmacokinetic behaviour may be improved by increased lipophilicity, listed by route of entry, are as follows:

1. Cell entry: drugs particularly likely to benefit are those that act primarily intracellularly. These include:
    a. All anti-inflammatory drugs, whether steroid or non-steroid
    b. All cytotoxic drugs used in the management of cancer;
    c. All antiviral drugs;
    d. All other drugs that have to enter cells in order to achieve optimum effects, in particular drugs which act on DNA or RNA, or on enzymes located intracellularly, or on second messenger systems, or on microtubules, mitochondria, lysosomes, or any other intracellular organelle.
    e. Steroid hormones and other hormones that act intracellularly, such as oestrogens, progestins, androgenic hormones and dehydroepiandrosterone.
2. Blood-brain barrier: all drugs acting on the central nervous system will have their transport improved by this technique. This includes all drugs used in psychiatry, all drugs used in cerebral infections with any organism or in cerebral cancer and all other drugs acting on nerve cells such as anti-epileptic drugs and others acting on neurological disorders such as multiple sclerosis, amyotrophic lateral sclerosis, Huntington's chorea and others.
3. Skin: as with the blood-brain barrier, all drugs that may be required to penetrate the skin to achieve a systemic effect will benefit from their conversion to a fatty acid derivative.

For example, the approach discussed is applicable to amino acids. Of particular interest are those which seem to play roles in the regulation of cell function as well as acting as components of proteins. Examples include tryptophan (a precursor of 5-hydroxytryptamine [5-HT], a key regular of nerve and muscle function), phenylalanine (a precursor of catecholamines) and arginine (a regulator of the synthesis of nitric oxide which also plays important roles in controlling cellular activities).

Properties Conferred Generally

Generally the compounds proposed herein have many advantages in addition to their lipophilicity. Two moieties of a given fatty acid or even a single moiety may be delivered, in a form which is readily incorporated into the body as an oral, parenteral or topical formation; which is very well tolerated with none of the side effects associated, for example, with free fatty acids; which is not too stable to be properly utilised.

When two different fatty acids are to be delivered, the advantages are as before plus the ability to administer simultaneously two materials with different biological actions in a single molecule. This avoids the regulatory problems which ensue when two materials are administered as separate compounds. When two drugs are delivered as separate molecules, regulatory authorities normally require each drug to be studied alone as well as in combination. If the two are combined in a single molecule, only the single molecule needs to be studied, greatly reducing the cost of development.

Where actives other than fatty acids are present there are similar advantages. The compounds allow drugs or other compounds to be administered in the form of relatively-lipophilic compounds which release the active moieties relatively easily, and which are well tolerated on oral, topical or parenteral administration. Their lipophilicity enables them to be absorbed partially through the lymphatic system, so by-passing the liver; to cause less gastrointestinal irritation than with many compounds; and to facilitate transport of drugs and other agents across lipophilic barriers such as the skin, the cell membrane and the blood-brain barrier.

There is evidence that interesting specific properties in addition to ready passage of lipid barriers can be conferred on many drugs by making them more lipophilic as outlined in scheme 1. These properties include prolonged duration of action, reduction of side effects especially gastro-intestinal, bypassing of first-pass liver metabolism and, potentially, site specific delivery of different materials.

Fatty Acid Derivatives; Effects of the Fatty Acids

The transport of actives across lipid membranes may be improved by linking them directly or via intermediate links to, in particular, gamma-linolenic acid (GLA) or dihomo-gamma-linolenic acid (DGLA), two fatty acids which in themselves have a range of desirable effects. These links also enable bioactive substances to be co-delivered in the same molecule with fatty acids which in themselves have desirable actions, irrespective of any transport advantages. Other fatty acids, such as any of the essential fatty acids (EFAs) and in particular the twelve natural acids of the n-6 and n-3 series EFAs (FIG. 1), can be used. Of these twelve, arachidonic acid, adrenic acid, stearidonic acid, eicosapentaenoic acid and docosahexaenoic acid are of particular interest because they in themselves have particularly desirable effects. Furthermore, any fatty acid, suitably $C_{12}$–$C_{30}$ or $C_{16}$–$C_{30}$ desirably with two or more cis or trans carbon-carbon double bonds may also be of use. Use may be in the form of the fatty acid or the corresponding fatty alcohol. Conjugated linoleic and columbinic acids are examples of fatty acids which in themselves have valuable properties and are likely to be of particular use. References to fatty acids are accordingly to be read herein as to be both forms, except where the chemistry of one or the other specifically is under discussion. The desirable properties of GLA and DGLA however, make them especially valuable for the purpose.

The essential fatty acids, which in nature are of the all—cis configuration, are systematically named as derivatives of the corresponding octadecanoic, eicosanoic or docosanoic acids, e.g. z,z-octadeca-9,12-dienoic acid or z,z,z,z,z,z-docosa-4,7,10,13,16,19-hexaenoic acid, but numerical designations based on the number of carbon atoms, the number of centres of unsaturation and the number of carbon atoms from the end of the chain to where the unsaturation begins, such as, correspondingly, 18:2m-6 or 22:6n-3 are convenient. Initials, e.g., EPA and shortened forms of the name e.g. eicosapentaenoic acid are used as trivial names in some of the cases.

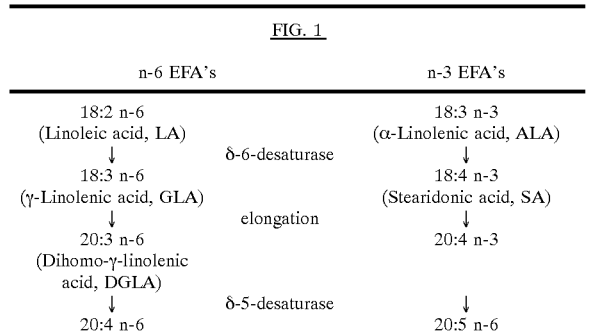

FIG. 1

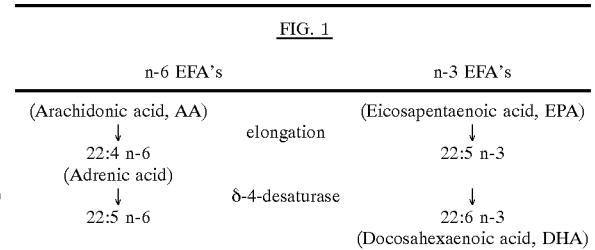

GLA and DGLA

In their own right GLA and DGLA have been shown to have anti-inflammatory effects, to lower blood pressure, to inhibit platelet aggregation, to lower cholesterol levels, to inhibit cancer cell growth, to reduce dyskinetic movements, to relieve breat pain, to improve calcium absorption and enhance its deposition in bone, to reduce the adverse effects of ionising radiation, to treat various psychiatric disorders, to cause vasodilation, to improve renal function, to treat the complications of diabetes, to dilate blood vessels and so on. Actives linked to GLA and DGLA will therefore not only become more lipophilic, enhancing penetration across all membranes, the skin and the blood brain barrier, but are also likely to exhibit new additional therapeutic effects.

Other fatty acis likely to be of especial value in this context are arachidonic acid and docosahexaenoic acid which are major constituents of all cell membranes; adrenic acid; and stearidonic acid and eicosapentaenoic acid which have ranges of desirable properties similar to those of GLA and DGLA. Fatty acids not included in the fatty acids of FIG. 1 which are of particular interest are conjugated linoleic acid (cLA) and columbinic acid (CA). cLA has a range of interesting effects in treating and preventing cancer, in promoting growth particularly of protein-containing tissues, in preventing and treating cardiovascular disease and as an antioxidant. CA has many of the properties of essential fatty acids.

Classes of Actives Having Mutual Efficacy with Bioactive Fatty Acids

Kinds of actives to be incorporated in compounds as set out herein may be broadly stated:
a) Drugs including antibiotics, antiprotozoals, antipsychotics, antidepressants and NSAIDs and compounds used in the treatment of cardiovascular, respiratory, dermatological, psychiatric, neurological, renal, muscular, gastrointestinal, reproductive and other diseases and in cancer.
b) Hormones
c) Amino acids
d) Vitamins particularly of the B group, and other essential nutrients.
e) Cytokines and peptides
f) Neurotransmitters and neurotransmitter precursors.
g) Phospholipid head groups such as inositol, choline, serine and ethanolamine, which may be linked directly or via the phosphate moiety.
h) Aromatic fatty acids as phenylacetic acid, phenyl butyric acid and cinnamic acid which are of particular value in cancer treatment.

Efficacy

The combination of the therapeutic effect of a drug with the therapeutic effect of a fatty acid may be considered through examples:

a) Psychotropic drugs may be linked to fatty acids such as GLA, DGLA, arachidonic acid, eicosapentaenoic or docosahexaenoic acid which have important roles in brain function, so providing a dual therapeutic effect.
b) Drugs used for the treatment of cardiovascular disease may be attached to a fatty acid which also has value in such treatment, such as eicosapentaenoic acid which lowers triglyceride levels and inhibits platelet aggregation, or GLA or DGLA which lower cholesterol levels and have vasodilator action, or arachidonic acid which is a potent cholesterol lowering agent, or DHA which has anti-arrhythmic properties.
c) Drugs used in the treatment of any form of inflammation may be linked to a fatty acid such as gammalinolenic acid, dihomo-gammalinolenic acid or eicosapentaenoic acid or docosahexaenoic acid which also has anti-inflammatory action.
d) Drugs used in the management of osteoporosis may be linked to GLA or DGLA which enhance the incorporation of calcium into bone, or to EPA or DHA which reduces urinary calcium excretion.
e) Drugs used in skin disease may be linked to GLA or DGLA which have anti-inflammatory effects on the skin.
f) Drugs used in cancer may be linked to GLA, DGLA, arachidonic acid, EPA or DHA which have anticancer effects in their own right and which may reverse resistance to anticancer drugs.

Concepts Applied to Essential Fatty Acids as Bioactives

The essential fatty acids (EFAs) as already referred to, and well known, consist of a series of twelve compounds. Although linoleic acid, the parent compound of the n-6 series, and alpha-linolenic acid, the parent compound of the n-3 series, are the main dietary EFAs, these substances as such have relatively minor roles in the body. In order to be fully useful to the body, the parent compounds must be metabolised to longer chain and more highly unsaturated compounds. In quantitative terms, as judged by their levels in cell membranes and in other lipid reactions dihomogammalinolenic acid (DGLA) and arachidonic acid (AA) are the main EFA metabolites of the n-6 series while eicosapentaenoic acid (EPA) and docosahexaenoic acid (DHA) are the main metabolites of the n-3 series. DGLA, AA, EPA and DHA are important constituents of most of the lipids in the body. As well as being important in themselves they can also give rise to a wide range of oxygenated derivatives, the eicosanoids, including the prostaglandins, leukotrienes and other compounds. The fatty acids likely to be of particular value in therapy are DGLA, AA, EPA and DHA, together with GLA, the precursor of DGLA, stearidonic acid (SA), the precursor of EPA and DPA (22:5n-3), the precursor of DHA, and adrenic acid.

Further there are fatty acids such as oleic acid, parinaric acid and columbinic acid that are not EFAs but may have significant effects in the body. One of the most interesting of these is conjugated linoleic acid which as noted earlier has a range of desirable effects.

It used to be though that, both in nutrition and in therapy of disease, it was sufficient to supply linoleic and alpha-linolenic acids and the body'own metabolism would do the rest. It is now widely accepted that this is not true. Different diseases may have different abnormal patterns of EFAs and because of problems in metabolism these cannot simply be corrected by giving linoleic or alpha-linolenic acid. It is therefore appropriate in many situations to provide increased amounts of one of the other EFAs or to give two or more of the EFAs simultaneously. While the EFAs can be supplied in various forms and in various mixtures, it is convenient in both nutrition and in medical treatment to be able to supply the fatty acids as particular molecules. Equally in various situations it may be desirable to give the EFA or other fatty acid in association with an amino acid, vitamin, drug or other molecule which in itself has desirable properties.

To date, proposals for administration of two fatty acids simultaneously have been in terms of particular triglycerides, following the natural occurrence of essential fatty acids in triglyceride form. However, triglycerides, unless symmetrical about the 2-carbon, are chiral and that fact, coupled with acyl migration between the alpha and beta positions makes the synthesis of specific triglycerides a difficult task. Such migration may take place after synthesis creating particular problems in a drug regulatory context. The lack of specificity when two fatty acids are present in the same triglyceride molecule creates many problems in synthesis, pharmacology, formulation and stability. Moreover triglycerides can be slow and difficult to synthesise.

For purposes of convenient administration of different fatty acids simultaneously or indeed of a single fatty acid in high amounts in well tolerated form, use can be made of the geminal tripartate mutual prodrug approach discussed earlier herein, and in detail later.

Chemical Nature Of Bioactives Which May Be Derivatised According To The Present Disclosure The present specification covers tripartate prodrugs in which unsaturated fatty acids and unsaturated fatty alcohols are linked to bioactives with an available carboxyl, alcohol, or acidic NH group through a geminal dioxo or geminal amino oxo linkage as appropriate.

Classes Of Bioactives By Chemistry (a) Bioactives with a free carboxyl group these may be derivatised as follows:
  (i) diester coupling with unsaturated fatty acid via geminal dioxo linkage

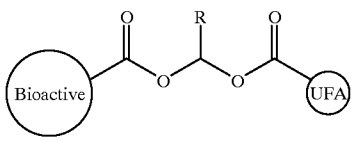

(ii) ester/ether coupling with unsaturated fatty alcohol via geminal dioxo linkage

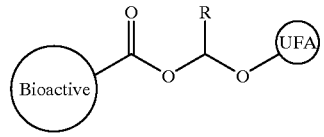

(b) bioactives with a free hydroxyl group—these may be dervatised as follows: ester/ether coupling with unsaturated fatty acid via geminal dioxo linkage

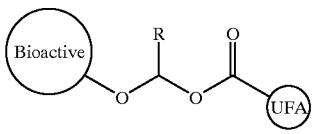

(c) bioactives with an acidic NH group (these include amides, imides, hydantoins, tertiary or N-heterocyclic amines and generally other NH acidic compounds)—these may be derivatives as follows:
  amino/ester coupling with unsaturated fatty acid via geminal amino oxo linkage

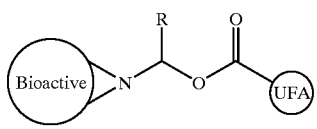

In all of these categories "unsaturated fatty acid" (and the derived "unsaturated fatty alcohol") represents a member of a group comprising oleic acid (and oleoyl alcohol) and any fatty acid (or corresponding fatty alcohol) with two or more cis or trans double bonds. However, the fatty acids likely to be of most value in this context are the essential fatty acids shown in FIG. 1 and in particular GLA, DGLA, AA, SA, EPA and DHA. For particular purposes conjugated linoleic acid and columbinic acid may be of great interest.

In all of these categories, R is either H, fully hydrocarbon in nature or containing heteroatoms (including ring substituted aromatics) corresponding with these definitions.

Represents the fatty acid alkyl chain corresponding with these definitions

General Discussion Of Synthesis

The individual fatty acids may be purified from natural animal, vegetable or microbial sources or may be chemically synthesised by methods known to those skilled in the art or developed hereafter.

The individual fatty alchohols may be prepared by chemical reduction of the fatty acids outlined above by methods known to those skilled in the art or developed hereafter.

Derivatisation of bioactives in classes (a), (b) and (c) may be carried out via the formation of an α-halogenated alkyl ester. Such chemistry may be achieved by any reasonable method of α-halogenated alkyl ester synthesis and especially:

(a) by reaction of an aldehyde, e.g. acetaldehyde, with acid halide in the presence of a Lewis acid, e.g. zinc chloride, at a temperature between 0° C. and 120° C. under an inert atmosphere.

Derviatisation of bioactives in classes (a) [ii] and (b) may be carried out via the formation of an α-halogenated alkyl ether. Such chemistry may be achieved by any reasonable method of α-halogenated alkyl ether synthesis and especially:

(b) by reaction of an aldehyde, e.g. acetaldehyde, with an alcohol in the presence of a hydrogen halide, e.g. hydrogen chloride, in a suitable inert solvent, e.g. dimethylformamide, at a temperature between 0° C. and 120° C. under an inert atmosphere.

Derivatisation of bioactives in class (c) may be carried out via the formation of an N-hydroxyalkylated compound. Such chemistry may be achieved by any reasonable method of N-hydroxyalkylation and especially:

(c) by reaction of an aldehyde e.g. acetaldehyde, with an acidic NH-compound, e.g. amide, in a suitable inert solvent, e.g. dimethylformamide, at a temperature between 0° C. and 120° C. under an inert atmosphere.

Derivatisation of bioactives in classes (a)[i] may be prepared by any reasonable synthesis of diesters linked by a geminal dioxo group and especially:

(d) by reaction of an α-halogenated alkyl ester with an acid in the presence of a suitable organic tertiary base, e.g. triethylamine, or a suitable inorganic base, e.g. potassium carbonate, in a suitable solvent, e.g. pyridine, at a temperature between 0° C. and 120° C. under an inert atmosphere.

Derivatisation of bioactives in class (a)[ii] and (b) may be prepared by any reasonable synthesis of ester/ether linked by a geminal dioxo group and especially:

(e) by reaction of an α-halogenated alkyl ester with an alcohol in the presence of a suitable orgainc tertiary base, e.g. triethylamine, or suitable inorganic base, e.g. potassium carbonate, in a suitable inert solvent, e.g. dimethylformamide, at a temperature between 0° C. and 120° C. under an inert atmosphere.

(f) by reaction of an α-halogenated alkyl ether with an acid in the presence of a suitable orgainc tertiary base, e.g. triethylamine, or suitable inorganic base, e.g. potassium carbonate, in a suitable inert solvent, e.g. dimethylformamide, at a temperature between 0° C. and 120° C. under an inert atmosphere.

Derivatisation of bioactives in class (c) may be prepared by any reasonable synthesis of amino/ester linked by a geminal amino oxo group and especially:

(g) by reaction of an α-halogenated alkyl ester with an acidic NH compound in the presence of a suitable organic tertiary base, e.g. triethylamine, or suitable inorganic base, e.g. potassium carbonate, in a suitable inert solvent, e.g. dimethylformamide, at a temperature between 0° C. and 120° C. under an inert atmosphere.

(h) by reaction of an N-hydroxyalkylated compound with acid chloride, acid anhydride or suitably activated ester with or without the presence of an organic tertiary base, e.g. pyridine, in a suitable inert solvent, e.g. dichloromethane, at a temperature between 0° C. and 120° C.

(i) by reaction of an N-hydroxyalkylated compound with acid in the presence of a condensing agent, e.g. 1,3-dicyclohexylcarbodiimide, with or without presence of a suitable organic tertiary base, e.g. 4-(N,N-dimethylaminopyridine), in an inert solvent, e.g. dichloromethane, at a temperature between 0° C. and 50° C.

(j) by reaction of alcohol with acid or acid, short or medium chain alkyl ester, or acid, activated ester, e.g. vinyl, in the presence of a hydrolase enzyme, e.g. hog liver esterase, with or without a suitable solvent, e.g. hexane, at temperatures between 20° and 80° C. under conditions such that the water or alcohol or aldehyde byproduct is removed, e.g. under vacuum.

Examples Of Pairs Of Actives Which May Be Linked Via The Geminal Tripartate Mutual Prodrug Link Examples of pairs of actives follow, the resulting compounds listed being, to our knowledge, novel. So far as that is so, they represent part of the invention as new chemical entities, as well as being novel in use in treatment or prevention of disease.

Fatty Acids

GLA-OA (OA=Oleic Acid), GLA-GLA, EPA-EPA, GLA-EPA, GLA-DHA, AA-DHA, AA-EPA, GLA-AA, GLA-SA, SA-DHA, AA-SA, DGLA-DGLA, DGLA-GLA, DGLA-SA, DGLA-AA, DGLA-EPA, DGLA-DHA, AA-AA, EPA-SA, EPA-DHA, DHA-DHA, cLA-cLA, cLA-GLA, cLA-DGLA, cLA-AA, cLA-SA, cLA-EPA, cLA-DHA, CA-CA, CA-GLA, CA-DGLA, CA-AA, CA-SA, CA-EPA, CA-DHA.

Vitamins

GLA-niacin, GLA-retinoic acid, GLA-retinol, GLA-pyridoxal, Di-GLA-pyridoxine, di-EPA-pyridoxal and in general any of e.g. GLA, DGLA, AA, SA, EPA or DHA with any vitamin including ascorbic acid, Vitamin D and its derivatives and analogues, Vitamin E and its derivatives and analogues, Vitamin K and its derivatives and analogues, Vitamin $B_1$ (thiamin), Vitamin $B_2$ (riboflavin), folic acid and related pterins, Vitamin $B_{12}$, biotin and pantothenic acid.

Amino Acids

GLA-tryptophan, GLA-proline, GLA-arginine, GLA- or DHA-phenylalanine GLA-GABA, GLA-aminolevulinic acid and in general any of e.g. GLA, DGLA, AA, SA, EPA or DHA with any natural amino acid or related compound such as taurine and carnitine.

Aromatic Acids

GLA-phenylbutyric acid, GLA-phenylacetic acid, GLA-trans-cinnamic acid and in general any of e.g. GLA, DGLA, AA, SA, EPA or DHA with any aryl alkanoic or aryl alkenoic acid.

Steroids

GLA-hydrocortisone, GLA-oestradiol, GLA- and DHA-dehydroepiandrosterone and in general any of e.g. GLA, DGLA, AA, SA, EPA or DHA with any natural or synthetic steroid, such as any oestrogen, any progestin, any adrenal steroid and any anti-inflammatory steroid, particularly betamethasone, prednisone, prednisolone, traimcinolone, budesonide, clobetasol, beclomethasone and other related steroids.

Anti-Oxidants

GLA-lipoic acid, DHA-lipoic acid, GLA-tocopherol, di-GLA-3,3'-thiodipropionic acid and in general any of e.g. GLA, DGLA, AA, SA, EPA or DHA with any natural or synthetic anti-oxidant with which they can be chemically linked. These include phenolic anti-oxidants (e.g. eugenol, carnosic acid, caffeic acid, BHT, gallic acid, tocopherols, tocotrienols and flavonoid anti-oxidants (e.g. myricetin, fisetin)), polyenes (e.g. retinoic acid), unsaturated sterols (e.g. $\Delta^5$-avenosterol), organosulfur compounds (e.g. allicin), terpenes (e.g. geraniol, abietic acid) and amino acid anti-oxidants (e.g. cysteine, carnosine).

Drugs

GLA and indomethacin, ibuprofen, fluoxetine, ampicillin, penicillin V, sulindac, salicylic acid, metronidazole, fluphenazine, dapsone, tranylcypromine, acetyl carnitine, haloperidol, mepacrine, chloroquine, penicillin, tetracycline, pravastatin, bisphosphonates such as efidronic acid, pamidronic acid and clordronic acid and their sodium salts, adenosylosuccinate and adenylosuccinate and related compounds and agents used as x-ray contrast media, and in general any of e.g. GLA, DGLA, AA, SA, EPA or DHA with any drug, particularly any drug used in the treatment of infections, inflammatory diseases, including various forms of arthritis, cancer, cardiovascular, respiratory, dermatological, psychiatric, neurological, muscular, renal, gastrointestinal, reproductive and other diseases.

The Present Invention

According to the present invention there are provided compounds containing geminal dioxo and geminal amino oxo linkages between bioactives containing free carboxyl groups and fatty alcohols and linkages between bioactives containing free carboxyl groups, free hydroxy groups and acidic NH groups and unsaturated fatty acids as discussed above in the section entitled "Classes of Bioactives by Chemistry". The present invention is particularly concerned with class (a)[i], geminal dioxo diesters of bioactives containing a free carboxyl group, i.e. compounds of the following structure:

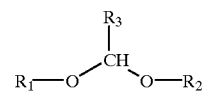

where $R_1$ is an acyl group derived from a $C_{16-30}$ fatty acid with two or more cis or trans double bonds and particularly an n-6 or n-3 series EFA or conjugated linoleic acid, or columbinic acid, or parinaric acid and $R_2$ is as $R_1$ the same or different, or any other nutrient, drug or other bioactive residue released as the active in the body and $R_3$ is either hydrogen, fully hydrocarbon, or containing heteroatoms, preferably an alkyl group particularly a $C_1$–$C_4$ alkyl group.

As a geminal dioxo diester, the general link is disclosed in the literature among many other geminal dioxo diesters but we have seen that its use in therapy in the form of an unsaturated fatty acid (UFA) geminal dioxo diester or as a compound with an UFA at one position and a bioactive (not being an unsaturated fatty acid) at the other, is both undisclosed and particularly significant. Indeed it offers a favourable way to give a singly fatty acid as the geminal dioxo diester. Further, apart from administering individual acids, such geminal dioxo diesters may have value in pharmaceutical formulation as emulsifiers.

The UFA geminal dioxo diesters have a wide variety of possible uses. They may be used as pharmaceuticals for the treatment or prevention of diseases in which abnormalities of fatty acids have been identified. They may be added to foods or added to or used as nutritional supplements for those who require the particular fatty acid for the treatment or prevention of diseases. They may also be used in foods or pharmaceuticals for veterinary use. They may further be used for skin care.

As advantages or in various particular aspects the invention provides:

(i) A convenient and safe way of asministering, for therapeutic or nutritional purposes, one or two unsaturated fatty acid moieties, or one unsaturated fatty acid and one bioactive that is not a fatty acid.

(ii) A derivative, of a bioactive required to cross lipid membranes in the body to exert its action whether in entry to a cell or in passing the skin, blood-brain or other barrier, through a geminal dioxo or geminal amino oxo linkage to an essential fatty acid of the natural n-6 or n-3 series and especially GLA or DGLA, AA, SA, EPA or DHA or the related fatty acids cLA or CA.

(iii) A fatty acid derivative of a drug such that the drug and fatty acid are mutually efficacious.

(iv) A method of improving the transport of a drug across lipid membranes in the body, characterises by the administration of the drug in a form as above.

(v) A method of manufacture of a medicament for improved therapy involving transport of a drug across lipid membranes in the body, characterised by incorporating the drug in a medicament in a form as above.

(vi) A method of manufacture of a medicament for delivering one or two fatty acids from the list in (ii) above or for delivering one of those fatty acids in association with another active agent.

Examples of specific compounds have been given earlier herein; synthesis examples come later.

Uses Generally

The fatty acids have a large number of desirable biological and therapeutic activities which have been detailed in numerous publications by the inventors and by others. Four of the fatty acids, GLA, DGLA, SA and EPA share a rather broad spectrum of effects which include:

1. Cardiovascular actions including vasodilatation, lowering of blood pressure, inhibition of platelet aggregation, lowering of triglyceride and LDL-cholesterol levels, elevation of HDL-cholesterol levels and inhibition of smooth muscle proliferation.
2. Anti-inflammatory actions including reduction of formation of pro-inflammatory mediators such as cytokines, and of eicosanoids derived from arachidonic acid, reduction of neutrophil migration and the neutrophil respiratory burst, reduction of local inflammatory responses, inhibition of inflammation in various animal models such as uric acid induced inflammation and adjuvant arthritis, and treatment of various inflammatory disorders such as osteoarthritis and rheumatoid arthritis.
3. Immunomodulatory functions including the damping down of excessive immune and allergic responses in animal models such as experimental allergic encephalomyelitis and uveitis, bronchial and cutaneous hyper-reactivity in sensitised animals, leading to the concept that they are of value in human diseases where excessive immune responses play a role.
4. Respiratory actions including bronchodilatation and inhibition of bronchoconstrictor actions.
5. Improvements in calcium balance with increased calcium absorption, reduced calcium excretion, increased deposition of calcium in bones and reduced ectopic deposition of calcium in tissues such as arteries and kidneys.
6. Anticancer effects of three sorts, selective cytotoxic damage and induction of apoptosis in cancer cells but not in normal cells, inhibition of growth by reduction of action of growth factors and interference with second messenger systems required for growth, inhibition of metastasis by various actions including increased expression of E-cadherins and inhibition of proteolytic enzymes such as urokinases, lipoxygenase and matrix metalloproteinases, and inhibition of cancer-associated cachexia.
7. Actions on nerve cells including maintenance of normal nerve membrane structure and fuction and the normal pre- and post-synaptic actions of neurotransmitters.

These desirable actions mean that this group of fatty acids can be used in the treatment of may different disorders including cardiovascular disorders of many types, inflammatory disorders including rheumatoid arthritis, osteoarthritis, ulcerative colitis and Chron's disease, respiratory disorders including asthma, psychiatric disorders including schizophrenia, alcoholism, attention deficit disorder, depression and Alzheimer's disease, neurological disorders including multiple sclerosis and Huntington's chorea, renal and urinary tract disorders including various types of renal inflammatory disease and urinary calcium stones, metabolic disorders including osteoporosis and ectopic calcification, and gastrointestinal ulcerative and inflammatory diseases. Although conjugated linoleic acid (cLA) has not been nearly as widely tested as, say GLA or EPA, it also seems to have a wide range of actions including effects valuable in the treatment of cancer, cardiovascular and metabolic diseases.

GLA, DGLA, AA and columbinic acid have desirable actions on the skin and are particularly valuable in the treatment of skin diseases such as atopic eczema, psoriasis, urticaria and allergic reactions.

AA is often regarded as a potentially harmful fatty acid. However, it is an essential constituent of all normal cell membranes and has been found to be present in low levels in various illnesses including atopic eczema, schizophrenia (Horrobin et al, Schizophrenia Res. 1994; 13: 195–207) and cardiovascular disorders (Horrobin, Prostaglandins Leukotr. EFAs 1995; 53: 385–96). AA is likely to be of particular value in these situations and also other psychiatric disorders such as alcoholism and attention deficit disorder where levels are also often low.

DHA shares some of the above actions of the EFAs but is found in particularly important amounts in cell membranes and especially in the membranes of the heart, the retina and the brain. DHA also has potent anti-inflammatory and desirable cardiovascular effect. DHA is likely to be of particular value in cardiovascular disorders, in retinal and visual disorders including retinitis pigmentosa, senile macular degeneration and dyslexia, and in psychiatric and neurological disorders including schizophrenia, attention deficit disorder, depression, alcoholism, Alzheimer's disease and other forms of dementia and multiple sclerosis.

Infections have also recently been identified as likely to respond to fatty acids, especially to GLA and DGLA, EPA and DHA. Many bacteria are killed by these fatty acids, including strains which are highly resistant to antibiotics, Recent work from a number of laboratories has also shown that these highly unsaturated fatty acids are important in successful responses to diseases like malaria and to protozoal diseases.

It is thus apparent that various specific fatty acids are likely to be able to add to the efficacy of drugs and other bioactive substances of almost any class, in both the treatment and prevention of disease, in skin care and in nutrition, as well as having valuable therapeutic effects when given in the form as now proposed by the present invention as a single fatty acid or as two different fatty acids in the same molecule. Of particular value in therapy is that under most circumstances the fatty acids are remarkably non-toxic and can be administered safely in large doses without the risk of important side effects.

Specific Uses of Compounds Containing Geminal Dioxo or Geminal Amino Oxo Linkage(s)

1. Geminal dioxo or geminal amino oxo moiety-containing compounds containing: two fatty acids in which one fatty acid is GLA or DGLA and the other is GLA, DGLA, SA, EPA, DHA, cLA (conjugated linoleic acid) or CA (columbinic acid) for the treatment of:
   (a) complications of diabetes, particularly neuropathy and retinopathy; and improvement of responses to insulin in diabetes and pre-diabetes;
   (b) cancers;
   (c) osteoarthritis;

(d) rheumatoid arthritis;
(e) other inflammatory and auto-immune diseases including Sjogren's syndrome, systemic lupus, ulcerative colitis, Crohn's disease and uveitis; respiratory diseases including asthma;
(g) neurological disorders including multiple sclerosis, Parkinson's disease and Huntington's chorea;
(h) renal and urinary tract disorders;
(i) cardiovascular disorders;
(j) degenerative diseases of the eye including retinitis pigmentosa and senile macular degeneration;
(k) psychiatric disorders including schizophrenia, Alzheimer's disease, attention deficit disorder, alcoholism and depression;
(l) prostatic hypertrophy and prostatitis;
(m) impotence and male infertility;
(n) mastalgia;
(o) male pattern baldness;
(p) osteoporosis;
(q) dermatological disorders, including atopic eczema, hand eczema, psoriasis, urticaria and allergic disorders;
(r) dyslexia and other learning disabilities;
(s) cancer cachexia.

2. Geminal dioxo or geminal amino oxo moiety-containing compounds containing two fatty acids in which one fatty acid is AA and the other is AA, GLA, DHA, DGLA or EPA for treatment of the disorders as at (1) above and especially (a), (g), (i), (j), (k), (q) and (r).

3. Geminal dioxo or geminal amino oxo moiety-containing compounds containing two fatty acids in which one fatty acid is EPA and the other is EPA or DHA for the treatment of any of the disorders as at (1) above but especially (b), (c), (d), (e), (f), (g), (h), (i), (j), (k), (p), (r) and (s).

4. Geminal dioxo or geminal amino oxo moiety-containing compounds in which one position is occupied by a fatty acid drawn from GLA, DGLA, AA, SA, cLA, EPA or DHA and the other position is occupied by an agent, selected from the following list, whose chemical structure is such that it can be linked by one of the linkages described herein:
 (a) tryptophan for the treatment of any disease but particularly for psychiatric, neurological, behavioural, pain and other disorders and especially depression, sleep and migraine;
 (b) phenylalanine for the treatment of any disease, but especially depression, multiple sclerosis and chronic fatigue syndrome;
 (c) arginine for the treatment of any disease but particularly diseases in which the production of nitric oxide is defective;
 (d) carnitine or carnitine derivatives for the treatment of any disease but especially muscle weakness, cardiac failure, chronic fatigue syndrome, Alzheimer's disease, and peripheral neuropathies;
 (e) any other amino acid or related substance for the treatment of any disease or aminolevulinic acid or derivative thereof for the treatment of any disease but especially cancers;
 (f) adenylosuccinate or related substances for the treatment of any disease but especially muscular dystrophy, cardiac failure, chronic fatigue and Alzheimer's disease and other dementias;
 (g) aspirin, salicylic acid, indomethacin, ibuprofen, or any other non-steroidal anti-inflammatory drug for the treatment of any disease but especially of inflammatory disorders of pain, of Alzheimer's disease and other dementias and of any disease in which platelet aggregation should be inhibited;
 (h) any antibiotic for the treatment of any appropriate infectious disease but especially tetracycline, clindamycin, minocycline, chlortetracycline and erythromycin for the treatment of acne;
 (i) any anti malarial or anti-protozoal drug for the treatment of any disease, but especially chloroquine, mepacrine, quinacrine and mefloquine for the treatment of malaria, protozoal disorders, inflammatory disorders and schizophrenia;
 (j) any antifungal drug for the treatment of any disease but especially metronidazole and antifungal imidazoles and nitroimidazoles and amphotericin for the treatment of fungal infections of various types;
 (k) any anti-inflammatory steroid for the treatment of any disease but especially hydrocordisone and betamethasone for the treatment of skin disorders and beclomethasone and budesonide for the treatment of asthma.
 (l) any gonadal steroid for the treatment of any disease but especially oestrogens and progestogens for the treatment of ovarian deficiency and osteoporosis and androgens for the treatment of testicular deficiency;
 (m) any adrenal steroid for the treatment of any disease, but especially dehydroepiandrosterone for the treatment of disorders associated with ageing;
 (n) any retinoid for the treatment of any disease but especially tretinoin and isotretinoin for the treatment of dermatological disorders and for use in skin care;
 (o) any anticancer agent for the treatment of cancer;
 (p) any antipsychotic agent for the treatment of schizophrenia and other psychoses;
 (q) any antidepressive agent for the treatment of any disease but especially for the treatment of depression;
 (r) any anti-anxiety agent for the treatment of any disease, but especially for the treatment of anxiety and panic attacks;
 (s) any immunosuppressive agent for the treatment of any disease but especially cyclosporine and tacrolimus for the control of immunity after organ transplantation and for the treatment of autoimmune and inflammatory disorders including psoriasis, eczema, asthma, rheumatoid arthritis and inflammatory bowel disease;
 (t) any proton pump inhibitor or H2 antagonist for the treatment of any disease but especially diseases associated with excess gastric acid production or reduced defenses against gastric acidity;
 (u) any diuretic for any disease, but especially for diseases associated with fluid retention and hypertension;
 (v) any calcium antagonist used for any disease but especially for cardiovascular diseases;
 (w) any angiotensin converting enzyme inhibitor or angiotensin antagonist used for any disease but especially for cardiovascular diseases;
 (x) any beta-blocker used for any disease but especially for cardiovascular disorders;
 (y) any antiepileptic drug used for any disease, but especially phenytoin, carbamazepine, valproate, ethosuximide, vigabatrin or lamotrigine for the treatment of epilepsy;
 (z) any hypolipidaemic agent for the treatment of any disease but especially fibrates and statins used for cholesterol lowering and cholesterol modification;

(aa) any oral hypoglycaemic or insulin-sensitising agents used in the management of diabetes;

(bb) any bisphosphonates used in the management of osteoporosis, Paget's disease or cancer;

(cc) any contrast agents used in radiology including diatrizoate compounds, iodipamide, ioglycamates, iopanoates, iophendylate, iothalamate, ioxaglate, metrizamide and related compounds;

(dd) any peptide or protein for use in the treatment of diseases for which the peptide or protein itself is used, including insulin, calcitonin, erythropoietin and other peptides;

(ee) any vitamin used in the treatment of any disease, or used in foods, nutritional supplements or food additives as a way of providing the vitamin effectively;

(ff) any antioxidant used in the management of any disease, but especially for those diseases in which antioxidants may be especially beneficial including cardiovascular diseases, cancer and inflammatory disorders and any antioxidant used as a food or other preservative or as a component of a food, food additive or nutritional supplement;

(gg) any porphyrin, chlorin or bacteriochlorin-based drug especially tetrakis(hydroxyphenyl) derivatives thereof used in photodynamic therapy of cancers.

Formulations

The fatty acid-bioactive geminal dioxo and amino oxo conjugates may be formulated in any way appropriate and which is known to those skilled in the art of preparing pharmaceuticals, skin care products or foods. They may be administered orally, enterally, topically, parenterally (subcutaneously, intramuscularly, intravenously), rectally, vaginally or by any other appropriate route.

Like triglycerides, fatty acid-bioactive geminal dioxo and amino oxo conjugates, especially those containing two fatty acids, may be readily emulsified using phospholipid or particularly galactolipid emulsifiers. Such emulsions are particularly useful for administration via oral, enteral and intravenous routes.

The doses of the actives to be administered largely range from 1 mg to 200 g per day, preferably 10 mg to 10 g and very preferably 10 mg to 3 g, according to their kind. In the treatment of cancer preferable doses may be in the 2–150 g/day range. They may be administered topically where appropriate in preparations where the actives form from 0.001% to 50% of the topical preparation, preferably 0.05% to 20% and very preferably 0.1% to 10%.

EXAMPLES

Illustrative syntheses of the linking of fatty acids and bioactives, through the geminal dioxo diester approach follow, with other generally illustrative material.

Example 1

α-(z,z,z-octadeca-6,9,12-trienoyloxy)-methyi-z,z,z-octadeca-6,9,12-trienoate (Geminal dioxo diester of GLA with GLA)

Part 1: α-chloromethyl z,z,z-octadeca-6,9,12-trienoate.

Anhydrous zinc chloride (26 mg) was added to a mixture of z,z,z-octadeca-6,9,12-trienoyl chloride (10.2 g) and paraformaldehyde (1.0 g). The mixture was stirred under an atmosphere of nitrogen at room temperature for 30 minutes. The reaction was then equipped with a reflux condenser and calcium chloride drying tube and heated at 90° C. for 6 hours. After completion of the reaction as shown by tlc, the mixture was diluted with hexane, filtered and purified by flash chromatography to give α-chloromethyl z,z,z-octadeca-6,9,12-trienoate as a clear oil.

Part 2: α-(z,z,z-octadeca-6,9,12-trienoyloxy)-methyl-z,z,z-octadeca-6,9,12-trienoate.

To a solution of z,z,z-octadeca-6,9,12-trienoic acid (85 mg) in 400 μl of dry pyridine with stirring in an atmosphere of nitrogen was added α-chloromethyl z,z,z-octadeca-6,9,12-trienoate (100 mg) and triethylamine (43 μl). The mixture was heated at 80° C. for 5 hours after which tlc indicated the reaction had gone to completion. The pyridine was evaporated and the residue dissolved in chloroform, washed with water, dried, concentrated and purified by flash column chromatography to give α-(z,z,z-octadeca-6,9,12-trienoyloxy)-methyl-z,z,z-octadeca-6,9,12-trienoate as a clear oil.

Example 2

α-(z,z,z-octadeca-6,9,12-trienoyloxy)-methyl-z,z,z,z,z-eicosa-5,8,11,14,17-pentaenoate (Geminal dioxo diester of GLA with EPA)

To a solution of z,z,z,z,z-eicosa-5,8,11,14,17-pentatnoic acid (104 mg) in 400 μl of dry pyridine with stirring in an atmosphere of nitrogen were added α-chloromethyl z,z,z-octadeca-6,9,12-trienoate (113 mg) and triethylamine (48 μl). The mixture was heated at 80° C. for 5 hours after which tlc indicated reaction had gone to completion. The pyridine was evaporated and the residue dissolved in chloroform and washed with water, dried, concentrated and purified by flash column chromatography to give α-(z,z,z-octadeca-6,9,12-trienoyloxy)-methyl-z,z,z,z,z-eicosa-5,8,11,14,17-pentaenoate as a clear oil.

Example 3

α-(z,z,z-octadeca-6,9,12-trienoyloxy)-methyl-1-(4-chlorobenzoyl)-5-methoxy-2-methylindole-3-acetate Geminal dioxo diester of GLA with indomethacin)

1-(4-chlorobenzoyl)-5-methoxy-2-methylindole-3-acetic acid (108 mg), αchloromethyl z,z,z-octadeca-6,9,12-trienoate (100 mg) and triethylamine (47 μl) were reacted in anhydrous pyridine (400 μl) as described in Example 1, Part 2. After flash chromatography α-(z,z,z-octadeca-6,9,12-trienoyloxy)-methyl-1-(4-chlorobenzoyl)-5-methoxy-2-methylindole-3-acetate was obtained as a clear oil.

Example 4

α-(z,z,z,z,z-eicosa-5,8,11,14,17-pentaenoyloxy)-methyl-1,2-dithiolane-3-pantanote.

Geminal dioxo diester of EPA with lipoic acid)

Part 1: α-chloromethyl z,z,z,z,z-eicosa-5,8,11,14,17-pentaenoate z,z,z,z,z-Eicosa-5,8,11,14,17-pentacnoic acid (9.1 g), paraformaldehyde (0.85 g) and zinc chloride (22 mg) were reacted together and purified as in Example 1, Part 1 to give α-chloromethyl z,z,z,z,z-eicosa-5,8,11,14,17-pentaenoate as a clear oil.

Part 2: α-z,z,z,z,z-eicosa-5,8,11,14,17-pentaenoyloxy)-methyl-1,2-dithiolane-3-pantanote.

1,2-Dithiolane-3-pentanoic acid (118 mg), α-chloromethyl z,z,z,z,z-eicosa-5,8,11,14,17-pentaenoate (100 mg) and hiethylamine (47 μl) were reacted in anhydrous pyridine (400 μl) as described in Example, 1, Part 2. After flash chromatography α-(z,z,z,z,z-eicosa-5,8,11,14,17-pentaenoyloxy)-methyl-1,2-dithiolane-3-pantanote was obtained as a clear oil.

Example 5

α-(z,z,z,z,z-eicosa-5,8,11,14,17-pentaenoyloxy)-methyl-2,3,5-triiodobenzoate

Geminal dioxo diester of EPA with triiodobenzoic acid)

2,3,5-Triiodobenzoic acid (285.6 mg), αchloromethyl z,z,z,z,z-eicosa-5,8,11,14,17-pentaenoate (200 mg) and triethylamine (80 μl) were reacted in anhydrous pyridine (400 μl) as described in Example, 1, Part 2. After flash chromatography α(z,z,z,z,z-eicosa-5,8,11,14,17-pentaenoyloxy)-methyl-1,2-dithiolane-3-pantanote was obtained as a clear oil.

Example 6

(±)-α-(z,z,z-octadeca-6,9,12-trienoyloxy-α-methyl)-methyl-2,3,5-triiodobenzoate

Geminal dioxo diester GLA with triiodobenzoic acid)

Part 1: (±)-α-chloroethyl z,z,z-octadeca-6,9,12-trienoate

Anhydrous zinc chloride (300 mg) was added to z,z,z-octadeca-6,9,12-trienoyl chloride (35.6 g). Acetaldehyde (5.2 g) was added dropwise with stirring over 30 minutes in an ice bath under an atmosphere of nitrogen. The reaction mixture was then stirred at room temperature for an additional 40 minutes and was shown to be complete by tlc. Water was added and the mixture was extracted twice with diethyl ether. After drying the solvent was evaporated to give (±)-α-chloroethyl z,z,z-octadeca-6,9,12-trienoate as a clear oil.

Part 2: (±)-α-(z,z,z-octadeca-6,9,12-trienoyloxy-α-methyl)-methyl-2,3,5-triiodobenzoate To a solution of 2,3,5-triiodobenzoic acid (220 mg) in 400 μl of dry pyridine and 200 μl of DMF with stirring in an atmosphere of nitrogen was added (±)-α-chloroethyl z,z,z-octadeca-6,9,12-trienoate (150 mg) and triethylamine (61 μl). The mixture was heated at 80° C. for 2.5 hours after which tlc indicated the reaction had gone to completion. The organic solvents were evaporated and the residue dissolved in chloroform, washed with water, dried, concentrated and purified by flash column chromatography to give (±)-α-(z,z,z-octadeca-6,9,12-trienoyloxy-α-methyl)-methyl-2,3,5-triiodobenzoate as a clear oil.

Example 7

(±)α-(z,z,z,z,z-eicosa-5,8,11,14,17-pentaenoyloxy-α-methyl)-methyl-1-(4-chlorobenzoyl)-5-methoxy-2-methylindole-3-acetate (Geminal dioxo diester of EPA with indomethacin)

Part 1: (±)-α-chloroethyl z,z,z,z,z-eicosa-5,8,11,14,17-pentaenoate z,z,z,z,z-Eicosa-5,8,11,14,17-pentaenoyl chloride (7 g), zinc chloride (51 mg) and acetaldehyde (0.92 g) were reacted together and purified as described in Example 6, Part 1 to give (±)-α-chloroethyl z,z,z,z, z-eicosa-5,8,11,14,17-pentaenoate as a clear oil.

Part 2: (±)-α-(z,z,z,z,z-eicosa-5,8,11,14,17-pentaenoyloxy-α-methyl)-methyl-1-(4-chlorobenzoyl)-5-methoxy-2-methylindole-3-acetate.

1-(4-chlorobenzoyl)-5-methoxy-2-methylindole-3-acetic acid (188 mg), (±)-α-chloroethyl z,z,z,z,z-eicosa-5,8,11,14,17-pentaenoate (200 mg) and triethylamine, (74 μl) were reacted for 5 hours in anhydrous pyridine (400 μl) as described in Example 6, Part 2. After purification by flash chromatography (±)-α-(z,z,z,z,z-eicosa-5,8,11,14,17-pentacaoyloxy-α-methyl)-methyl-1-(4-chlorobenzoyl)-5-methoxy-2-methylindole-3-acetate was obtained as a clear oil.

What is claimed is:

1. A compound having the following structure

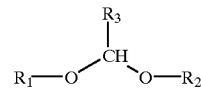

where $R_1$ is an acyl group derived from a $C_{16-30}$ fatty acid with two or more cis or trans double bonds and $R_2$ is a nutrient, drug or other bioactive residue as the active in the body and $R_3$ is either hydrogen of gydrocarbyl, with the proviso that $R_2$ is not the residue of nicotinic acid.

2. A compound according to claim 1 wherein said fatty acid is an n-6 or n-3 series EFA or conjugated linoleic acid, or columbinic acid, or parinaric acid.

3. A compound according to claim 1 wherein the fatty acid is gamma-linolenic acid, dihomo-gamma-linolenic acid, arachidonic acid, adrenic acid, stearidonic acid, eicosapentaenoic acid, docosapentaenoic acid n-3 or docosahexaenoic acid.

4. A compound according to claim 1, 2 or 3 wherein $R_3$ is an alkyl group.

5. A compound according to claim 1, 2 or 3 wherein $R_3$ is a $C_1$–$C_4$ alkyl group.

6. A compound according to any of claims 1 to 3 where $R_2$ is a drug or other active required to cross lipid membranes in the body to exert its action whether in entry to or movement within a cell in which it is to act, or in passing the skin, blood-brain or other barrier.

7. A compound according to any of claims 1 to 3 wherein $R_2$ is a drug, vitamin, amino acid, anti-oxidant or other active which is required to have an action additive to complementary to or synergistic with $R_1$.

8. A method of manufacturing a medicament for improving the transport of a drug or other active across lipid membranes in the body or securing an action as set out in claim 7, characterised by use of the active in the form of a compound as in any preceding claim.

9. A method of improving the transport of a drug or other active across lipid membranes in the body, characterised by use of the active in the form of a compound as set out in claim 1.

10. The compound according to claim 1, where $R_1$ is an acyl moiety corresponding to an acid selected from the group consisting of λ-linolenic acid (GLA), dihomo-λ-linolenic acid (DGLA), arachidonic acid (AA), stearidonic acid (SA), eicosapentaenoic acid (EPA), docosahexaenoic acid (DHA), and conjugated linoleic acid (cLA) and $R_2$ is a nutrient, drug, or other bioactive residue selected from the group consisting of amino acids, adenylsuccinate or derivatives thereof, nonsteroidal antiinflammatory drugs, antibiotics, antimalarial or antiprotozoal drugs, antifungal drugs, antiinflammatory steroids, gonadal steroids, adrenal steroids, retinoids, anticancer agents, antipsychotic agents, antidepressive agents, antianxiety agents, immunosuppressive agents, proton pump inhibitors or H2 antagonists, diuretics, calcium antagonists, angiotensin converting enzyme inhibitors or angiotensin antagonists, beta-adrenergic blockers, antiepileptic drugs, hypolipidaemic agents, oral hypoglycaemics or insulin-sensitizing agents, bisphosphonates, radiological contrast agents, peptides or proteins, vitamins, antioxidants, and porphyrin, chlorin, or bacteriochlorin-based drugs.

11. The compound according to claim 10, wherein $R_2$ is the residue of an amino acid selected from the group consisting of tryptophan, phenylalanine, arginine, carnitine or derivatives thereof, and aminolevulinic acid.

12. The compound according to claim 10, wherein $R_2$ is the residue of adenylosuccinate or derivative thereof.

13. The compound according to claim 10, wherein $R_2$ is the residue of a nonsteroidal antiinflammatory drug selected from the group consisting of aspirin, salicylic acid, indomethacin, and ibuprofen.

14. The compound according to claim 10, wherein $R_2$ is the residue of an antibiotic selected from the group consisting of tetracycline, clindamycin, minocycline, chlortetracycline, and erythromycin.

15. The compound according to claim 10, wherein $R_2$ is the residue of an antimalarial or antiprotozoal drug selected from the group consisting of chloroquine, mepacrine, quinacrine and mefloquine.

16. The compound according to claim 10, wherein $R_2$ is the residue of an antifungal drug selected from the group consisting of metronidazole, antifungal imidazoles and nitroimidazoles, and amphotericin.

17. The compound according to claim 10, wherein $R_2$ is the residue of an antiinflammatory steroid selected from the group consisting of hydrocortisone, betamethasone, beclomethasone, and budesonide.

18. The compound according to claim 10, wherein $R_2$ is the residue of a gonadal steroid selected from the group consisting of oestrogens, progestogens, and androgens.

19. The compound according to claim 10, wherein $R_2$ is the residue of an adrenal steroid.

20. The compound according to claim 19, wherein the adrenal steroid is dehydroepiandrosterone.

21. The compound according to claim 10, wherein $R_2$ is the residue of a retinoid selected from the group consisting of tretinoin and isotretinoin.

22. The compound according to claim 10, wherein $R_2$ is the residue of an immunosuppressive agent selected from the group consisting of cyclosporin and tacrolimus.

23. The compound according to claim 10, wherein $R_2$ is the residue of an antiepileptic drug selected from the group consisting of phenytoin, carbamazepine, valproate, ethosuximide, vigabatrin, and lamotrigine.

24. The compound according to claim 10, wherein $R_2$ is the residue of a hypolipidaemic agent selected from the group consisting of fibrates and statins.

25. The compound according to claim 10, wherein $R_2$ is the residue of a radiological contrast agent selected from the group consisting of diatrizoate compounds, iodipamide, ioglycamates, iopanoates, iophendylate, iothalamate, ioxaglate, metrizamide, and derivatives thereof.

26. The compound according to claim 10, wherein $R_2$ is the residue of a peptide or protein selected from the group consisting of insulin, calcitonin, and erythropoietin.

27. The compound according to claim 10, wherein $R_2$ is the residue of a porphyrin, chlorin, or bacteriochlorin-based drug or tetrakis(hydroxyphenyl) derivatives thereof.

28. A method for treating a disorder selected from the group consisting of complications of diabetes; cancer; osteoarthritis; rheumatoid arthritis; inflammatory and autoimmune diseases other than arthritis; respiratory diseases; neurological disorders; renal and urinary tract disorders; cardiovascular disorders; degenerative diseases of the eye; psychiatric disorders; prostatic hypertrophy and prostatitis; impotence and male infertility; mastalgia; male pattern baldness; osteoporosis; dermatological disorders; dyslexia and other learning disabilities; and cancer cachexia; comprising administering to a patient in need thereof an effective amount of the compound of claim 10.

29. The method according to claim 28, wherein said disorder is a complication of diabetes selected from the group consisting of neuropathy, retinopathy, and insufficient response to insulin.

30. The method according to claim 28, wherein said disorder is an inflammatory and autoimmune disease other than arthritis selected from the group consisting of Sjogren's syndrome, systemic lupus, ulcerative colitis, Crohn's disease, and uveitis.

31. The method according to claim 28, wherein said disorder is asthma.

32. The method according to claim 28, wherein said disorder is a neurological disorder selected from the group consisting of multiple sclerosis, Parkinson's disease, and Huntington's chorea.

33. The method according to claim 28, wherein said disorder is a degenerative disease of the eye selected from the group consisting of retinitis pigmentosa and senile macular degeneration.

34. The method according to claim 28, wherein said disorder is a psychiatric disorder selected from the group consisting of schizophrenia, Alzheimer's disease, attention deficit disorder, alcoholism, and depression.

35. The method according to claim 28, wherein said disorder is a dermatological disorder selected from the group consisting of atopic eczema, hand eczema, psoriasis, urticaria, and allergic disorders.

36. The method according to claim 28, wherein said disorder is selected from the group consisting of complications of diabetes; neurological disorders; cardiovascular disorders; degenerative diseases of the eye; psychiatric disorders; dermatological disorders; and dyslexia and other learning disabilities; and wherein $R^1$ is arachidonic acid (AA) and $R^2$ is selected from the group consisting of λ-linolenic acid (GLA), dihomo-λ-linolenic acid (DGLA), arachidonic acid (AA), eicosapentaenoic acid (EPA), and docosahexaenoic acid (DHA).

37. The method according to claim 28, wherein said disorder is selected from the group consisting of cancer; osteoarthritis; rheumatoid arthritis; inflammatory and autoimmune diseases other than arthritis; respiratory diseases; neurological disorders; renal and urinary tract disorders; cardiovascular disorders; degenerative diseases of the eye; psychiatric disorders; osteoporosis; dermatological disorders; dyslexia and other learning disabilities; and cancer cachexia; and wherein $R^1$ is eicosapentaenoic acid (EPA) and $R_2$ is selected from the group consisting of eicosapentaenoic acid (EPA) and docosahexaenoic acid (DHA).

38. The method according to claim 28, wherein said administering comprises oral, topical, enteral or parenteral administration.

39. A method of treating or preventing a nutritional deficiency, comprising administering to a patient in need thereof an effective amount of a compound according to claim 10.

40. The method according to claim 39, wherein administering comprises oral administration of a composition comprising said compound and a food, nutritional supplement, or food additive.

41. The method according to claim 39, said administering comprises enteral or parenteral administration.

42. A cosmetic composition comprising a compound according to claim 10 in combination with a carrier suitable for application to the hair or skin.

43. A method for treating skin disorders comprising applying to the skin or hair of a patient in need thereof the composition of claim 39.

44. A method for treating psychiatric, neurological, behavioral, steep, or pain disorders comprising administering to a patient in need thereof an effective amount of the compound of claim 11, wherein said amino acid is tryptophan.

45. The method according to claim 44, wherein said disorders comprise depression or migraine.

46. A method for treating depression, multiple sclerosis, or chronic fatigue syndrome comprising administering to a patient in need thereof an effective amount of the compound of claim 11, wherein said amino acid is phenylalanine.

47. A method for treating diseases associated with defective nitric oxide production, comprising administering to a patient in need thereof an effective amount of the compound of claim 11, wherein said amino acid is arginine.

48. A method for treating muscle weakness, cardiac failure, chronic fatigue syndrome, Alzheimer's disease, or peripheral neuropathies, comprising administering to a patient in need thereof an effective amount of the compound of claim 11, wherein said amino acid is carnitine or a carnitine derivative.

49. A method for treating cancer comprising administering to a patient in need thereof an effective amount of the compound of claim 11, wherein said amino acid is aminolevulinic acid.

50. A method for treating muscular dystrophy, cardiac failure, chronic fatigue syndrome, or Alzheimer's disease, comprising administering to a patient in need thereof an effective amount of the compound of claim 12.

51. A method for treating inflammatory disorders of pain, Alzheimer's disease, or for inhibiting platelet aggregation, comprising administering to a patient in need thereof an effective amount of the compound of claim 13.

52. A method of treating or preventing a bacterial infection, comprising administering to a patient in need thereof an effective amount of the compound of claim 14.

53. The method according to claim 52, wherein said bacterial infection comprises acne.

54. The method of treating malaria, protozoal disorders, inflammatory disorders, or schizophrenia, comprising administering to a patient in need thereof an effective amount of the compound of claim 15.

55. A method for treating fungal infections, comprising administering to a patient in need thereof an effective amount of the compound of claim 16.

56. A method for treating skin disorders or asthma, comprising administering to a patient in need thereof an effective amount of the compound of claim 17.

57. A method for treating ovarian deficiency, osteoporosis or testicular deficiency, comprising administering to a patient in need thereof an effective amount of the compound of claim 18.

58. A method of treating disorders associated with aging comprising administering to a patient in need thereof an effective amount of the compound of claim 19.

59. A method for treating dermatological disorders, comprising administering to a patient in need thereof an effective amount of the compound of claim 21.

60. A method for treating autoimmune and inflammatory disorders comprising administering to a patient in need thereof an effective amount of the compound of claim 22.

61. The method according to claim 60, wherein said autoimmune or inflammatory disorders are selected from the group consisting of psoriasis, eczema, asthma, rheumatoid arthritis, and inflammatory bowel disease.

62. A method for treating epilepsy, comprising administering to a patient in need thereof an effective amount of the compound of claim 23.

63. A method of lowering cholesterol level, comprising administering to a patient in need thereof an effective amount of the compound of claim 24.

64. A method for treating cancer cachexia, comprising administering to a patient in need thereof an effective amount of the compound of claim 10.

\* \* \* \* \*